(12) United States Patent
Yamakawa (10) Patent No.: US 10,056,248 B2
(45) Date of Patent: Aug. 21, 2018

(54) METHOD FOR MEASURING OVERALL CONCENTRATION OF OXIDIZING SUBSTANCES, SUBSTRATE CLEANING METHOD, AND SUBSTRATE CLEANING SYSTEM

(71) Applicant: KURITA WATER INDUSTRIES LTD., Nakano-ku, Tokyo (JP)

(72) Inventor: Haruyoshi Yamakawa, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 241 days.

(21) Appl. No.: 14/903,538

(22) PCT Filed: Jun. 23, 2014

(86) PCT No.: PCT/JP2014/066522
§ 371 (c)(1),
(2) Date: Jan. 7, 2016

(87) PCT Pub. No.: WO2015/012041
PCT Pub. Date: Jan. 29, 2015

(65) Prior Publication Data
US 2016/0172185 A1    Jun. 16, 2016

(30) Foreign Application Priority Data

Jul. 23, 2013    (JP) .................................. 2013-152603

(51) Int. Cl.
*G01N 21/00* (2006.01)
*H01L 21/02* (2006.01)
(Continued)

(52) U.S. Cl.
CPC .......... *H01L 21/02057* (2013.01); *B08B 3/04* (2013.01); *C25B 1/30* (2013.01);
(Continued)

(58) Field of Classification Search
None
See application file for complete search history.

(56) References Cited

U.S. PATENT DOCUMENTS

2008/0251108 A1    10/2008 Nagai et al.
2013/0313129 A1    11/2013 Kosaka et al.

FOREIGN PATENT DOCUMENTS

| JP | 2006114880 A | 4/2006 |
|---|---|---|
| JP | 2006278687 A | 10/2006 |

(Continued)

OTHER PUBLICATIONS

International Search Report (ISR) dated Sep. 9, 2014 issued in International Application No. PCT/P2014/066522.

*Primary Examiner* — Xiaoyun R Xu
(74) *Attorney, Agent, or Firm* — Holtz, Holtz & Volek PC (57) ABSTRACT

To allow online monitoring of the overall concentration of oxidizing substances in electrolyzed sulfuric acid, for example, in a cleaning system, absorbance data having undergone baseline correction in relation to the overall concentration of oxidizing substances by using a standard sample liquid in the form of an electrolyzed sulfuric acid preparation liquid having the same sulfuric acid concentration as the sulfuric acid concentration of the electrolyzed sulfuric acid is prepared, and absorbance is measured over wavelengths ranging from 190 to 290 nm by using a sample liquid in the form of electrolyzed sulfuric acid having a sulfuric acid concentration ranging from 60 to 97% by mass and a liquid temperature ranging from 20 to 70° C. to measure the overall concentration of oxidizing substances in the electrolyzed sulfuric acid on the basis of the data. The overall concentration of oxidizing substances in the electrolyzed sulfuric acid can thus be immediately measured.

5 Claims, 5 Drawing Sheets

(51) Int. Cl.
*G01N 21/33* (2006.01)
*B08B 3/04* (2006.01)
*C25B 1/30* (2006.01)
*C25B 9/00* (2006.01)
*C25B 15/02* (2006.01)
*C25B 15/08* (2006.01)
*G01N 21/25* (2006.01)
*H01L 21/67* (2006.01)
*H01L 21/66* (2006.01)
*G01N 21/27* (2006.01)

(52) U.S. Cl.
CPC ................ *C25B 9/00* (2013.01); *C25B 15/02* (2013.01); *C25B 15/08* (2013.01); *G01N 21/255* (2013.01); *G01N 21/274* (2013.01); *G01N 21/33* (2013.01); *H01L 21/6704* (2013.01); *H01L 21/67017* (2013.01); *H01L 21/67253* (2013.01); *H01L 22/10* (2013.01); *G01N 2201/127* (2013.01)

(56) References Cited

FOREIGN PATENT DOCUMENTS

| | | |
|---|---|---|
| JP | 2008164504 A | 7/2008 |
| JP | 2012184951 A | 9/2012 |
| JP | 2012189320 A | 10/2012 |
| WO | 2012118022 A1 | 9/2012 |

METHOD FOR MEASURING OVERALL CONCENTRATION OF OXIDIZING SUBSTANCES, SUBSTRATE CLEANING METHOD, AND SUBSTRATE CLEANING SYSTEM

TECHNICAL FIELD

The present invention relates to a measurement method for quantifying an oxidant in electrolyzed sulfuric acid produced by electrolysis of sulfuric acid, a substrate cleaning method, and a substrate cleaning system.

BACKGROUND ART

In a resist separation step carried out in related art, a solution called SPM (sulfuric acid-hydrogen peroxide mixture), which is a combination of concentrated sulfuric acid and hydrogen peroxide water, is used. The method consumes a large amount of sulfuric acid and hydrogen peroxide water and is therefore disadvantageous in that the method incurs high running cost and a large amount of liquid waste is produced. To address the disadvantages, the present inventors have already developed a cleaning method and a cleaning system in which electrolyzed sulfuric acid containing an oxidizing substance, such as persulfuric acid, produced by electrolysis of sulfuric acid is used as a cleaning liquid and sulfuric acid is cyclically used (see Patent Literatures 1 and 2, for example). The cleaning system allows reduction in the amount of chemical liquid to be used and the amount of liquid waste to be produced and further provides a high cleaning effect.

CITATION LIST

Patent Literature

Patent Literature 1
  Japanese Patent Laid-Open No. 2006-114880
Patent Literature 2
  Japanese Patent Laid-Open No. 2006-278687
Patent Literature 3
  Japanese Patent Laid-Open No. 2008-164504
Patent Literature 4
  Japanese Patent Laid-Open No. 2012-184951

SUMMARY OF INVENTION

Technical Problem

In a resist step, the concentrations of sulfuric acid and other substances in a chemical liquid greatly affect a cleaning effect. For example, as a method for measuring the concentration of an oxidant in electrolyzed sulfuric acid, Patent Literature 3 discloses a measuring method on the basis of titrimetric analysis using an oxidation-reduction reaction, which is a method that readily allows measurement of the concentration of an oxidant in electrolyzed sulfuric acid. The method is, however, what is called offline measurement in which a fraction of liquid to be measured is collected, a titration operation period is required, and a post-measurement liquid cannot be recovered because it is contaminated with a titrant. Patent Literature 4, for example, discloses a densitometer for measuring the total concentration of oxidizing substances. However, the method disclosed in Patent Literature 4, in which it is necessary to heat a liquid to be measured in advance, is problematic in that it takes time before the measurement starts and the densitometer has a complicated apparatus configuration.

An object of the invention of the present application is to provide overall oxidizing substance concentration measurement method for measuring all oxidizing substances in electrolyzed sulfuric acid in a short period and therefore allowing online monitoring of all the oxidizing substances, a substrate cleaning method, and a substrate cleaning system.

Solution to Problem

That is, among methods for measuring an overall concentration of oxidizing substances according to the present embodiment, a first present invention relates to a method for measuring an overall concentration of oxidizing substances in electrolyzed sulfuric acid, the method characterized in that absorbance data having undergone baseline correction in relation to the overall concentration of oxidizing substances by using a standard sample liquid in the form of an electrolyzed sulfuric acid preparation liquid having the same sulfuric acid concentration as the sulfuric acid concentration of the electrolyzed sulfuric acid is prepared, and absorbance is measured over wavelengths ranging from 190 to 290 nm by using a sample liquid in the form of electrolyzed sulfuric acid having a sulfuric acid concentration ranging from 60 to 97% by mass and a liquid temperature ranging from 20 to 70° C. to measure the overall concentration of oxidizing substances in the electrolyzed sulfuric acid on the basis of the data.

A method for measuring the overall concentration of oxidizing substances according to a second present invention is characterized in that in the first present invention, the oxidizing substances include peroxomonosulfuric acid, peroxodisulfuric acid, and hydrogen peroxide.

A substrate cleaning method according to a third present invention is a substrate cleaning method in which a sulfuric acid solution is circulated while electrolyzed to increase electrolysis concentration and an electrolyzed sulfuric acid solution having the increased electrolysis concentration is used to clean a semiconductor substrate, the method characterized in that the electrolyzed sulfuric acid is measured by using the measurement method according to the first or second invention, and an overall concentration of oxidizing substances in the electrolyzed sulfuric acid solution is monitored online.

A substrate cleaning method according to a fourth present invention is characterized in that in the third present invention, before the electrolyzed sulfuric acid comes into contact with the substrate, part of the electrolyzed sulfuric acid is branched as a sample liquid from a substrate cleaning system for absorbance measurement, and the sample liquid after the measurement is returned to the substrate cleaning system.

A substrate cleaning method according to a fifth present invention is characterized in that in the third or fourth present invention, waste of the cleaning liquid used to clean the substrate is not circulated to be reused but is discarded, part of the electrolyzed sulfuric acid is branched as a sample liquid in any intermediate position of a supply line through which the electrolyzed sulfuric acid solution is supplied for the substrate cleaning from a line through which the electrolyzed liquid is circulated, absorbance measurement is performed on the sample liquid to measure the overall concentration of the oxidizing substances, and after the measurement, in a position upstream of the substrate being cleaned, the sample liquid is returned to the substrate cleaning system.

A substrate cleaning method according to a sixth present invention is characterized in that in the fifth present invention, the electrolyzed sulfuric acid after the measurement is returned to a position upstream of the position where the electrolyzed sulfuric acid is branched from the supply line.

A substrate cleaning system according to a seventh present invention is characterized in that the substrate cleaning system comprises: an electrolysis apparatus that electrolyzes a sulfuric acid solution;

a circulation line which is provided with the electrolysis apparatus and through which the sulfuric acid solution is circulated while electrolyzed by the electrolysis apparatus;

a substrate cleaning apparatus that uses the electrolyzed sulfuric acid to clean a semiconductor substrate;

a supply line through which the electrolyzed sulfuric acid is delivered to the substrate cleaning apparatus;

an absorption photometer;

a storage section that holds absorbance data having undergone baseline correction in relation to the overall concentration of oxidizing substances by using a standard sample liquid in the form of an electrolyzed sulfuric acid preparation liquid having the same sulfuric acid concentration as the sulfuric acid concentration of the electrolyzed sulfuric acid;

a branch line that extracts part of the electrolyzed sulfuric acid from any of the electrolysis apparatus, the circulation line, and the supply line and delivers the extracted electrolyzed sulfuric acid to the absorption photometer; and a measurement apparatus that measures the overall concentration of oxidizing substances in the electrolyzed sulfuric acid solution based not only on data obtained by the absorption photometer that measures absorbance over wavelengths ranging from 190 to 290 nm by using a sample liquid in the form of the electrolyzed sulfuric acid having a sulfuric acid concentration ranging from 60 to 97% by mass and a liquid temperature ranging from 20 to 70° C. but also on the data having undergone the baseline correction.

The invention of the present application allows online measurement of the concentration of oxidizing substance present in a cleaning liquid for removing contaminants from an electronic material, such as a substrate, and cleaning the electronic material. By using an online monitor or the like to which the method of the invention of the present application is applied in a cleaning method or in a cleaning system, the performance of a cleaning apparatus can be managed.

Electrolyzed sulfuric acid produced by electrolysis of sulfuric acid contains oxidizing substances, such as peroxodisulfuric acid, peroxomonosulfuric acid, and hydrogen peroxide in the form of a mixture. Peroxodisulfuric acid, peroxomonosulfuric acid, and hydrogen peroxide each have an absorption peak at wavelengths ranging from about 190 to 290 nm but differ from one another in terms of molar absorptivity. The overall amount of the oxidizing substances usually cannot be known when they are present in the form of a mixture. However, since these oxidizing substances are present in balanced states in electrolyzed sulfuric acid, as shown in the following Expressions (2) and (3), the proportions of the oxidizing substances present in the form of a mixture are roughly fixed when the concentration of the sulfuric acid ranges from 60 to 97 mass % and the temperature of the sulfuric acid ranges from room temperature to about 70° C. on the basis of the equilibrium relationship. In view of the fact described above, the overall amount of the oxidizing substances can be measured on the basis of absorbance even when the oxidizing substances are present in the form of a mixture.

$$H_2S_2O_8 + H_2O \leftrightarrow H_2SO_5 + H_2SO_4 \quad (2)$$

$$H_2SO_5 + H_2O \leftrightarrow H_2O_2 + H_2SO_4 \quad (3)$$

On the basis of the consideration described above, a calibration relationship among the concentration of sulfuric acid, the temperature of the sulfuric acid, absorption magnitude, and the overall concentration of oxidizing substances is determined in advance on the basis, for example, of manually analyzed iodine titration method (method including the steps of adding an aqueous potassium iodide solution to a solution containing oxidizing substances, performing titration using a sodium thiosulfate solution having a known concentration, which serves as a titrant, on iodine released in the oxidation-reduction reaction between the aqueous potassium iodide solution and the oxidizing substances, and measuring the overall concentration of the oxidizing substances) and absorption photometry, and in the field, absorption magnitude of electrolyzed sulfuric acid having a constant sulfuric acid concentration and a constant liquid temperature is measured with a densitometer according to the present invention. The overall concentration of the oxidizing substances contained in the electrolyzed sulfuric acid is then calculated on the basis of the calibration relationship described above (it is, however, noted that baseline correction is performed for the difference in sulfuric acid concentration in advance). In the invention of the present application, the calibration relationship derived on the basis of the relationship with the absorbance is not necessarily determined by the iodine titration method described above and is instead determined, for example, by potential difference measurement.

Advantageous Effects of Invention

That is, according to the invention of the present application, the overall concentration of oxidizing substances in electrolyzed sulfuric acid can be measured in a short period by preparing, in advance, absorbance data having undergone baseline correction in correspondence with the overall concentration of oxidizing substances by using a standard sample liquid in the form of an electrolyzed sulfuric acid preparation liquid having the same sulfuric acid concentration as the sulfuric acid concentration of the electrolyzed sulfuric acid and measuring absorbance over wavelengths ranging from 190 to 290 nm by using a sample liquid in the form of electrolyzed sulfuric acid having a predetermined concentration and a predetermined temperature. Further, online monitoring using a result of the measurement can be performed. The sample liquid used in the measurement can be recovered and reused as desired.

DESCRIPTION OF EMBODIMENTS

The present invention relates to an analysis method for measuring an oxidant present in electrolyzed sulfuric acid having a known sulfuric acid concentration by using absorbance in an ultraviolet range from 190 to 290 nm and further relates to an apparatus that performs online monitoring of the concentration of the oxidant without discharging the liquid having been measured. The absorbance is desirably limited to a value in a single spectrum.

When sulfuric acid of at least 60% by mass is electrolyzed, peroxodisulfuric acid is produced in accordance with the following reaction formula (1):

Further, the peroxodisulfuric acid produces peroxomonosulfuric acid in the equilibrium reaction expressed by Expression (2), and the peroxomonosulfuric acid produces hydrogen peroxide in the equilibrium reaction expressed by Expression (3). Therefore, although oxidizing substances, such as peroxodisulfuric acid, peroxomonosulfuric acid, and hydrogen peroxide are present in the form of a mixture in the sulfuric acid electrolyte, each of the oxidizing substances can be quantified, for example, by using an iodine titration method, whereby the overall concentration of oxidizing substances can be known by using the present titration method. In the description, peroxodisulfuric acid and peroxomonosulfuric acid are collectively called persulfuric acid.

The iodine titration method is a method including the steps of adding an aqueous potassium iodide solution to a solution containing oxidizing substances, performing titration using a sodium thiosulfate solution having a known concentration, which serves as a titrant, on iodine released in the oxidation-reduction reaction between the aqueous potassium iodide solution and the oxidizing substances, and measuring the overall concentration of the oxidizing substances. In the measurement method, however, since it is necessary to add the titrant to a sampled solution and perform titration, it takes time to perform the measurement and the solution after the analysis needs to be discarded. The measurement method therefore does not allow online measurement.

In the present invention, sulfuric acid of known concentration is used, or the concentration of sulfuric acid is measured in advance with an analyzer separate from the apparatus according to the invention, and the absorbance of a liquid under measurement is measured without any preprocessing, such as heating, to measure the overall concentration of oxidizing substances. Peroxodisulfuric acid, peroxomonosulfuric acid, and hydrogen peroxide, which are oxidizing substances contained in the liquid under measurement, each have an absorption peak at wavelengths ranging from about 190 to 290 nm but differ from one another in terms of molar absorptivity. The overall amount of the oxidizing substances cannot be known when they are present in the form of a mixture. However, since these oxidants are present in balanced states in electrolyzed sulfuric acid, as shown in Expressions (2) and (3), the proportions of the oxidizing substances present in the form of a mixture are roughly fixed at a predetermined sulfuric acid concentration, that is, at a predetermined ratio between the sulfuric acid and water, and at a temperature ranging from room temperature to about 70° C. Among all oxidizing substances in typical electrolyzed sulfuric acid, peroxodisulfuric acid, peroxomonosulfuric acid, and hydrogen peroxide as a whole, which are primary components, account for 95% by mass immediately after the electrolysis, and the proportion thereof tends to further increase with time.

Experimental Example

Solutions having sulfuric acid concentrations of 70%, 85%, and 92% by mass were electrolyzed by using conductive diamond electrodes at room temperature with the amount of applied current being 10 [Ah/L] into electrolyzed sulfuric acid solutions, and the solutions immediately after the electrolysis were gradually heated at a speed of 40 [° C./hr] to 70° C. The concentrations of the oxidants immediately after the electrolysis were measured to be 38 [mM], 26 [mM], and 11 [mM].

Figure 1:
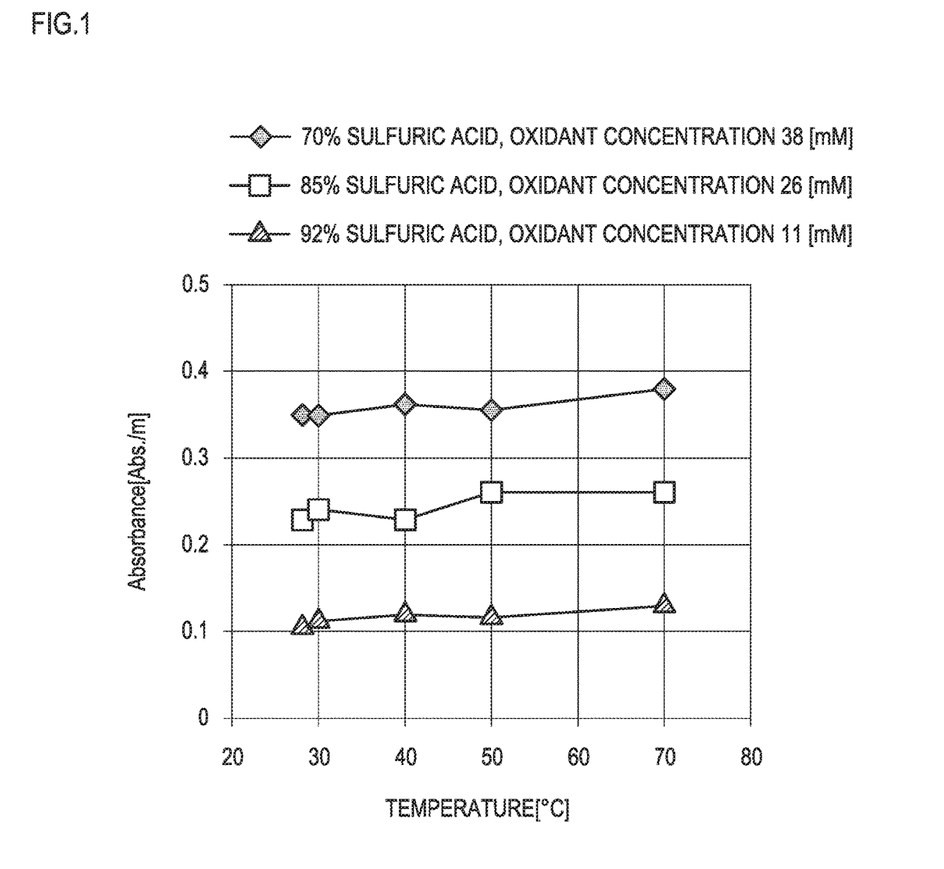
FIG. 1 shows graphs illustrating the relationship among the concentration of electrolyzed sulfuric acid solution, the temperature of the solution, and absorbance in an embodiment of the present invention.

As a result of measurement of absorbance at 30° C., 40° C., 50° C., and 70° C., an effect of the changes in temperature on the absorbance is hardly recognized, as shown in FIG. 1. It can therefore be concluded that in electrolyzed sulfuric acid having a sulfuric acid concentration ranging from 70 to 92% by mass, the proportions of the oxidizing substances present immediately after the electrolysis are roughly fixed over the temperature range from room temperature to 70° C.

Therefore, knowing the sulfuric acid concentration in advance and measuring the absorbance over wavelengths ranging from 190 to 290 nm over which absorption takes place allow the measured absorbance to correlate with concentration obtained by the iodine titration method. Using a pipe made of a fluororesin-based material as a member that comes into contact with a liquid in an apparatus for measuring the absorbance and using quartz to form an absorbance measurement cell prevent impurities from contaminating the solution after the measurement, whereby the liquid does not need to be discarded as desired but can be used for the intended purpose.

In the present invention, it is not necessary to specify a specific method as a method for measuring the sulfuric acid concentration. A method on the basis of sonic speed measurement, a method on the basis of resonant vibration, or any other method that allows online measurement can be employed. Further, a method for determining the oxidant concentration may either be a method for calculating the oxidant concentration from the sulfuric acid concentration and the absorption magnitude of a liquid under measurement or a method for measuring the relationship between the absorption magnitude and the oxidant concentration at a predetermined sulfuric acid concentration in advance and measuring the oxidant concentration only at the predetermined sulfuric acid concentration. Using the principle of the present invention allows online monitoring of the oxidant concentration in the sulfuric acid electrolysis apparatus.

In the present embodiment, a plurality of absorption spectra are not measured, but only a single absorption spectrum is measured for measurement of the overall concentration of oxidizing substances. In this case, presence of impurities greatly affects a result of the measurement. A cleaning system that circulates electrolyzed sulfuric acid, in which impurities tend to coexist, undesirably provides a limited degree of advantageous effect of the measurement technology of the present invention. The reason for this is that in any applications, such as resist separation, residual metal removal, and selective etching, the measurement is affected by coexisting impurities as along as circulation occurs, resulting in inaccurate measurement. Therefore, in practice, it is desirable, in a cleaning-liquid-discarded, single-substrate cleaning system that does not circulate cleaning liquid waste to reproduce and reuse the cleaning liquid, that an analyzer is installed in a line branched from an electrolyzed sulfuric acid supply line or any other line before the cleaning liquid is heated to a cleaning temperature.

<Measurement of Absorption Spectrum>

To measure an absorption spectrum, in general, the same sample (typically water or buffer liquid) is placed both in a sample cell and a control cell, and the absorbance is recorded versus wavelengths. The records are called a baseline, which is a straight line representing zero absorbance in principle. However, insufficient matching between cells being used, a small amount of dirt or scratch of the cell, variation in intensity of a light beam, deviation in incident angle of light under measurement that is incident on a detector, and other factors produce irregularities of the baseline. In most commercially available self-recording spectrophotometers, the baseline is first stored in a computer in the main body of a measurement apparatus, and correction is made assuming that the baseline corresponds to zero absorbance. A sample to be measured is then placed in the sample cell, and the measurement is performed with the wavelength swept. A resultant curve is subtracted from the absorption curve for the control sample (baseline) to produce an absorption spectrum of the sample.

In the present embodiment, when the sulfuric acid concentration of a cleaning liquid for cleaning an object to be cleaned is determined, the absorbance can be measured by using a sulfuric acid solution having the set sulfuric acid concentration as the baseline.

A substrate cleaning system in FIG. 2 will next be described.

A substrate cleaning system 1 includes an electrolysis apparatus 2, which supplies a sulfuric acid solution and electrolyzes the sulfuric acid solution, and a storage tank 3, which stores the sulfuric acid solution (including electrolyzed sulfuric acid solution after electrolysis), with the electrolysis apparatus 2 and the storage tank 3 connected to each other via a circulation line 4.

The electrolysis apparatus 2 is a diaphragmless apparatus in which an anode and a cathode are accommodated with no diaphragm therebetween, and a DC power supply that is not shown is connected to the electrodes. It is desirable to form both the anode and the cathode or at least the anode in such a way that a portion thereof that comes into contact with the sulfuric acid solution is made of diamond. The electrolysis apparatus according to the present invention can be configured as a diaphragm-type apparatus, may include a bipolar electrode, or may have a configuration in which the bipolar electrode is formed of a diamond electrode.

A delivery-side circulation line 4 from the storage tank 3 to the electrolysis apparatus 2 are provided with a liquid delivery pump 5 and a cooler 6 in this order. A return-side circulation line 4 from the electrolysis apparatus 2 to the storage tank 3 is provided with a gas/liquid separation tank 7.

To the storage tank 3 are connected a pure water supply line 8, through which pure water is introduced into the storage tank 3, and a concentrated sulfuric acid supply line 9, through which concentrated sulfuric acid is introduced into the storage tank 3, whereby pure water and concentrated sulfuric acid can be supplied to the storage tank 3 when the system is started or in operation. When they are supplied in operation, the sulfuric acid concentration in the storage tank can be adjusted.

To the storage tank 3 is further connected a supply line 10, which is provided with a persulfuric acid delivery pump 11, and the front end of the supply line 10 is connected to a single-substrate cleaning apparatus 20 via a heater 17. The heater 17 is preferably a one-pass-type heater. It is desirable to adjust the temperature of the solution in the storage tank 3 at a value ranging from 50 to 90° C.

A filter 12 and a preheat tank 13 are connected in this order to the supply line 10 between the persulfuric acid delivery pump 11 and the heater 17. The filter 12 captures and removes particles contained in the persulfuric-acid-containing sulfuric acid solution being delivered. The preheat tank 13 stores and heats the solution delivered from the storage tank 3. The preheat tank 13 heats the solution, for example, to a temperature ranging from 90 to 120° C.

Further, a branch line 14, which extracts part of the electrolyzed solution flowing through the supply line 10, is branched from and connected to the supply line 10 between the preheat tank 13 and the heater 17, and the branch line 14 is connected to an oxidant concentration monitoring apparatus 15. The solution introduced into the oxidant concentration monitoring apparatus 15 is directed through a return line 16 to the supply line 10 between the preheat tank 13 and the heater 17 but upstream of the branched position or to the preheat tank 13. The oxidant concentration monitoring apparatus 15 corresponds to a measurement apparatus in the present invention and includes an absorption photometer 15a, a nonvolatile storage section 15b, which holds absorbance data having undergone baseline correction in relation to the overall concentration of oxidizing substances by using a standard sample liquid in the form of an electrolyzed sulfuric acid preparation liquid having the same sulfuric acid concentration as the sulfuric acid concentration of the electrolyzed sulfuric acid, and a controller 15c, which controls the entire oxidant concentration monitoring apparatus 15. The storage section 15b can, for example, be a flash memory, an HDD, or a removable USB memory.

In the single-substrate cleaning apparatus 20, the cleaning solution supplied through the supply line 10 is sprayed, dropped, or caused to flow down onto a semiconductor substrate 100 placed in the single-substrate cleaning apparatus 20. In the dropping or flowing-down operation, the solution may be pressurized and sprayed onto the semiconductor substrate 100.

To the single-substrate cleaning apparatus 20 is connected a drain line 21, through which the solution in the apparatus is drained, and the drain line 21 is branched into an extra-system discharge line 22 and a recovery line 23. An unused solution recovery tank 24 is connected to the recovery line 23. The drain line 21 is so configured that the drain used in a cleaning process is caused to flow through the drain line 21 and the extra-system discharge line 22 connected to each other, for example, through valve operation and discharged out of the system. On the other hand, the cleaning liquid not having used in the cleaning process is caused to flow through the drain line 21 and the recovery line 23 connected to each other, for example, through valve operation and recovered into the unused solution recovery tank 24.

A return line 25 is connected to the unused solution recovery tank 24, and the front side of the return line 25 is connected to the storage tank 3.

Further, the return line 25 from the unused solution recovery tank 24 to the storage tank 3 is provided with a circulating liquid delivery pump 26, a filter 27, and a cooler 28 in this order.

The oxidant concentration monitoring apparatus 15 will next be described.

In the oxidant concentration monitoring apparatus 15, the storage section 14b holds, in advance, absorbance data having undergone baseline correction in relation to the overall concentration of oxidizing substances by using a standard sample liquid in the form of an electrolyzed sulfuric acid preparation liquid having the same sulfuric acid concentration as that of the electrolyzed sulfuric acid introduced through the branch line 14. The sulfuric acid concentration described above ranges from 60 to 97% by mass, and the temperature of the sulfuric acid ranges from 20 to 70° C., and the wavelength is selected from the range from 190 to 290 nm. As for the sulfuric acid concentration, a value prepared in the storage tank 3 in advance is used. The solution temperature of the electrolyzed sulfuric acid can be acquired by measurement using a thermometer (not shown) provided in the preheat tank 13 or measurement using a thermometer (not shown) provided in the oxidant concentration monitoring apparatus 15.

As for the absorbance data, for example, the overall mass of the oxidizing substances can be acquired by using a manually analyzed iodine titration method, and the relationship between the overall mass of the oxidizing substances and the absorbance can be determined in advance. Specifically, an aqueous potassium iodide solution is added to a solution containing oxidizing substances, and titration using a sodium thiosulfate solution having a known concentration, which serves as a titrant, is performed on iodine released in the oxidation-reduction reaction between the aqueous potassium iodide solution and the oxidizing substances, followed by measurement of the overall concentration of the oxidizing substances. The relationship among the sulfuric acid concentration, the absorbance over the wavelengths ranging from 190 to 290 nm, and the overall mass of the oxidizing substances is then acquired as data.

The operation of the cleaning system 1 described above will next be described.

The storage tank 3 stores the sulfuric acid solution having the sulfuric acid concentration ranging from 60 to 97% by mass. The sulfuric acid concentration can be adjusted by adjusting the amounts of the solutions supplied through the pure water supply line 8 and the concentrated sulfuric acid supply line 9.

The sulfuric acid solution described above is delivered by the liquid delivery pump 5 through the circulation line 4 and introduced to the liquid input side of the electrolysis apparatus 2. In the electrolysis apparatus 2, the DC power supply electrifies the anode and the cathode so that the sulfuric acid solution introduced into the electrolysis apparatus 2 is electrolyzed. In the electrolysis apparatus 1, the electrolysis produces oxidizing substances including persulfuric acid at the anode.

The oxidizing substances in the form of a mixture with the sulfuric acid solution described above are returned toward the storage tank 3 through the circulation line 4. At this point, gases produced in the electrolysis operation are separated by the gas/liquid separator 7. The electrolyzed sulfuric acid solution forms electrolyzed sulfuric acid containing persulfuric acid and other oxidizing substances, is returned through the circulation line 4 to the storage tank 3, and then repeatedly delivered to the electrolysis apparatus 2. The sulfuric acid solution is cooled as required by the cooler 6 when it is delivered to the electrolysis apparatus 2, and the sulfuric acid solution cooled to a temperature ranging, for example, from 30 to 70° C. is introduced into the electrolysis apparatus 2.

After the electrolyzed sulfuric acid is introduced into the storage tank 3, part of the electrolyzed sulfuric acid is delivered by the liquid delivery pump 11 through the supply line 10 at an appropriate point of time. The electrolyzed sulfuric acid flowing through the supply line 10 is, after the filter 12 captures and removes particles from the electrolyzed sulfuric acid, introduced into the preheat tank 13, which heats the electrolyzed sulfuric acid to a temperature ranging, for example, from 90 to 120° C.

The electrolyzed sulfuric acid in the preheat tank 13 is delivered through the supply line 10 to the heater 17, which heats the electrolyzed sulfuric acid to a temperature ranging, for example, from 140 to 220° C. The electrolyzed sulfuric acid is caused to come into contact with the semiconductor substrate 100, for example, in one minute after the heating for cleaning on a substrate basis. The cleaning liquid used in the cleaning process is, after coming into contact with the semiconductor substrate 100, discharged out of the system and discarded through the drain line 21 and the extra-system discharge line 22.

At an appropriate point of time during the cleaning, all the time, or before the cleaning, part of the electrolyzed sulfuric acid is extracted from the supply line 10 or a relay tank that is not shown but is provided on the supply line 10 in a position between the outlet of the preheat tank 13 and the inlet of the heater 17 and introduced through the branch line 14 to the oxidant concentration monitoring apparatus 15. In the oxidant concentration monitoring apparatus 15, it is checked that the introduced electrolyzed sulfuric acid has a temperature ranging from 20 to 70° C., and the absorption photometer 15a measures the absorbance in a single spectrum over wavelengths ranging from 190 to 290 nm. From the sulfuric acid concentration at this point and a result of the absorbance measurement, corresponding overall concentration of the oxidizing substances is acquired. The acquired overall concentration of the oxidizing substances can be printed or otherwise displayed by a display or a printer that is not shown. On the basis of the acquired overall concentration of the oxidizing substances, the electrolysis conditions in the electrolysis apparatus 2, the electrolyzed sulfuric acid delivery timing in the persulfuric acid delivery pump 11, the amount of electrolyzed sulfuric acid to be delivered, the placement of the semiconductor substrate 100, and other factors can be adjusted to achieve a state suitable for the cleaning. The electrolysis conditions, the electrolyzed sulfuric acid delivery timing, the amount of electrolyzed sulfuric acid to be delivered, the placement of the semiconductor substrate 100, and other factors can be controlled via the controller 15c, which is controlled in accordance with the acquired overall concentration of the oxidizing substances. Instead, the electrolysis conditions, the electrolyzed sulfuric acid delivery timing, the amount of electrolyzed sulfuric acid to be delivered, the placement, and other factors may be manually adjusted in accordance with the acquired overall concentration of the oxidizing substances.

The electrolyzed sulfuric acid introduced into the oxidant concentration monitoring apparatus 15 is returned to the preheat tank 13 through the return line 16 and allowed to be reused. Instead, the electrolyzed sulfuric acid introduced into the oxidant concentration monitoring apparatus 15 may be returned to the supply line 10 between the preheat tank 13 and the heater 17 but in a position upstream of the branch position and then reused.

In the present embodiment, the position where the electrolyzed sulfuric acid used to measure the oxidant concentration is returned is not limited to a specific position, but it is desirable that the electrolyzed sulfuric acid is returned to a position upstream of the measurement point. The electrolyzed sulfuric acid used in the measurement can thus be reused with influence thereof on the system suppressed.

EXAMPLES

Example 1

Figure 3:
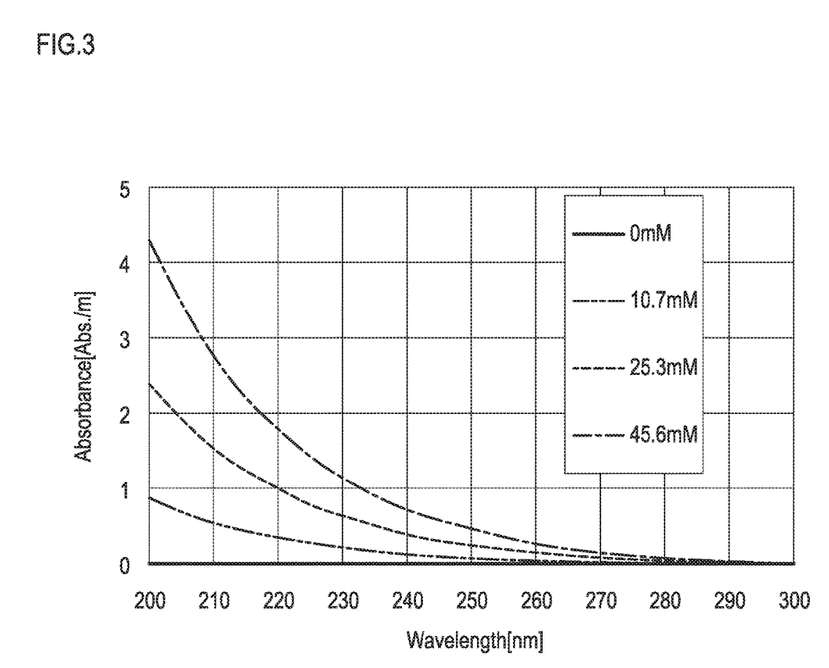
FIG. 3 shows the relationship between the overall mass of oxidizing substances and absorbance versus wavelength in the embodiment of the present invention.

Electrolyzed sulfuric acid solutions containing oxidants having different concentrations produced by electrolysis of sulfuric acid adjusted to have a concentration of 80% by mass were caused to undergo measurement of absorption magnitude over 200 to 300 nm with respect to the baseline absorption magnitude associated with the 80-mass % sulfuric acid. The oxidant concentration was analyzed by the iodine titration method. The electrolyzed sulfuric acid solutions were produced under the following electrolysis conditions: A conductive diamond electrode was used as each of the anode and the cathode; and the amount of applied current was set at 0, 5, 10, and 15 [Ah/L]. FIG. 3 shows spectra associated with the electrolyzed sulfuric acid solutions. As shown in FIG. 3, the higher the oxidant concentration, the higher the absorption magnitude in the region from 200 to 300 nm.

Figure 4:
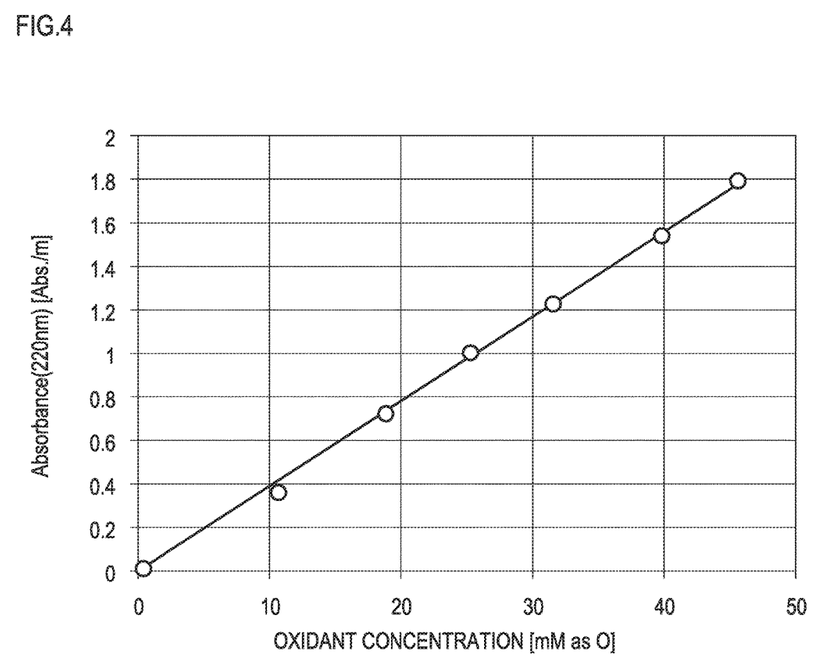
FIG. 4 shows the relationship between the overall mass of oxidizing substances and absorbance at a specific wavelength in the embodiment of the present invention.

FIG. 4 shows the relationship between the oxidant concentration and the absorption magnitude at 220 nm. FIG. 4 indicates that the oxidant concentration and the absorption magnitude highly correlate with each other.

Example 2

Figure 2:
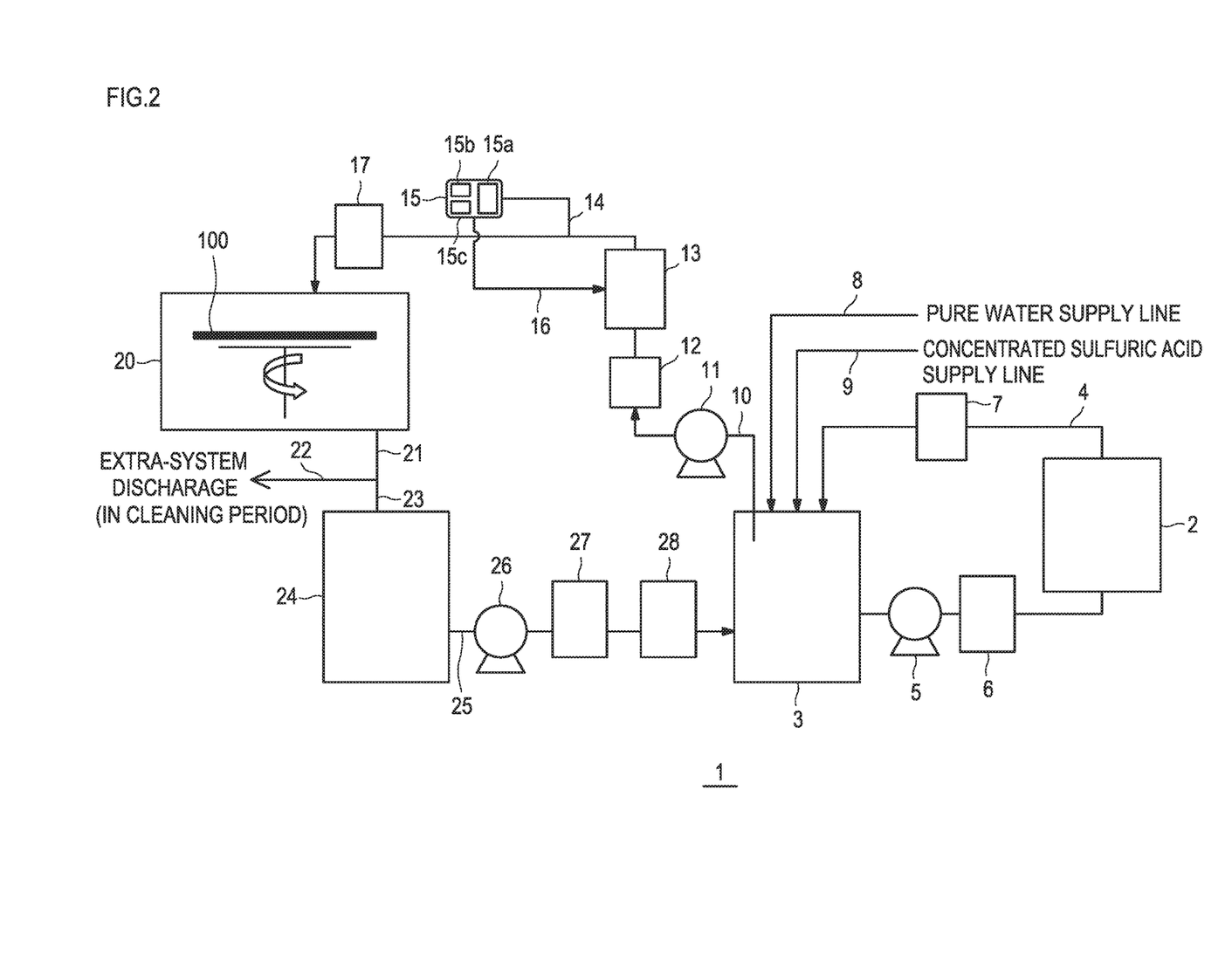
FIG. 2 schematically shows a cleaning system in the embodiment of the present invention.
Figure 5:
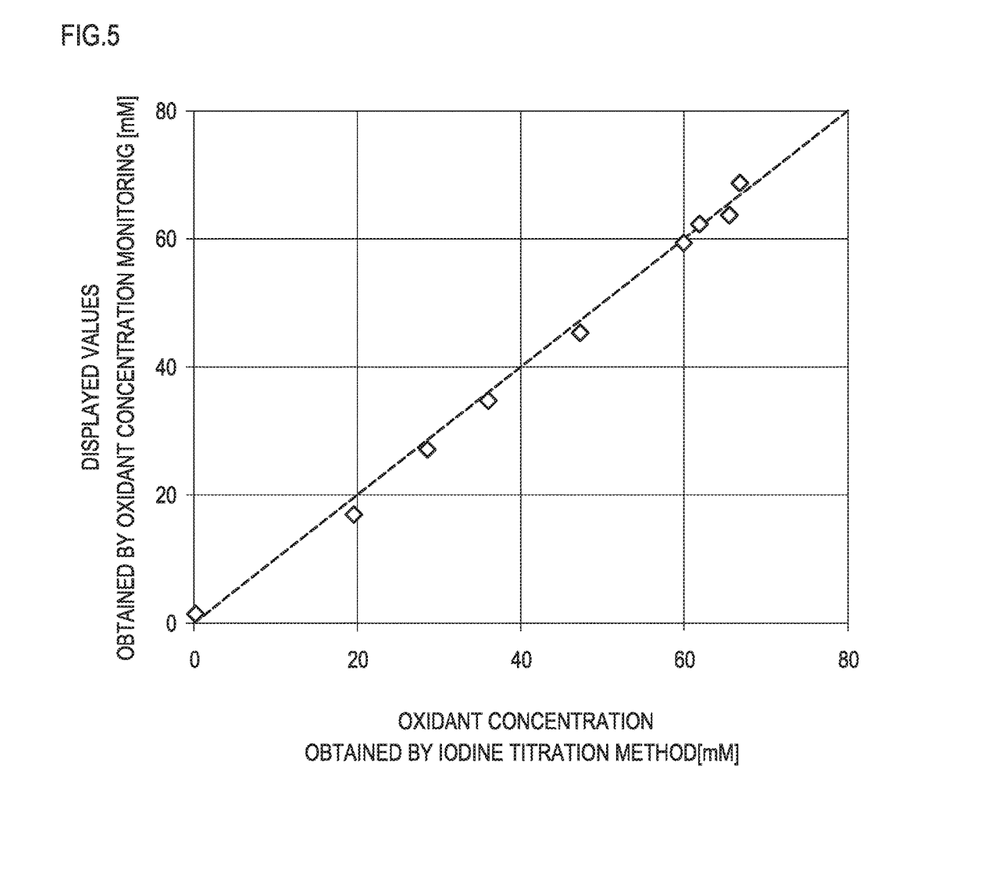
FIG. 5 shows the relationship between the overall mass of the oxidizing substances obtained by an iodine titration method and display values obtained by concentration monitoring in the embodiment of the present invention.

The apparatus shown in FIG. 2 was operated to achieve a point where the oxidant concentration was stable. In this state, comparison between the iodine titration method and the oxidant concentration monitoring using the absorbance was performed. The apparatus was operated under the condition of the sulfuric acid concentration being 80% by mass, and the sulfuric acid supplied to the cleaning apparatus was all returned to the sulfuric acid electrolysis apparatus. The amount of applied current was 280 Ah/L, and the overall amount of stored electrolyzed sulfuric acid was set at 80 L. The oxidant concentration monitoring apparatus measured the absorption magnitude at 254 nm in absorbance, and the baseline was set on the basis of the sulfuric acid concentration of 80% by mass. For five hours since the apparatus was activated, the measurement was performed every 30 minutes. FIG. 5 shows a result of the measurement. It is ascertained from the result that measurements obtained by the oxidant concentration monitoring using absorbance roughly coincide with those obtained by the iodine titration method.

REFERENCE SIGNS LIST

1 Cleaning system
2 Electrolysis apparatus
3 Storage tank
4 Circulation line
10 Supply line
13 Preheat tank
14 Branch line
15 Oxidant concentration monitoring apparatus
15a Absorption photometer
16 Return line
15b Storage section
20 Single-substrate cleaning apparatus

The invention claimed is:

1. A substrate cleaning method of a substrate cleaning system in which a sulfuric acid solution is circulated while electrolyzed to increase electrolysis concentration and an electrolyzed sulfuric acid solution having the increased electrolysis concentration is used to clean a semiconductor substrate, the method comprising:
   preparing absorbance data having undergone baseline correction in relation to overall concentration of oxidizing substances by using a standard sample liquid in the form of an electrolyzed sulfuric acid preparation liquid having the same sulfuric acid concentration as the sulfuric acid concentration of the electrolyzed sulfuric acid solution; and
   measuring absorbance over wavelengths ranging from 190 to 290 nm by using a sample liquid in chemical equilibrium in the form of the electrolyzed sulfuric acid solution having a sulfuric acid concentration ranging from 60 to 97% by mass and a liquid temperature ranging from 20 to 70° C. to measure the overall concentration of oxidizing substances in the electrolyzed sulfuric acid solution based on the prepared data,
   wherein the overall concentration of oxidizing substances in the electrolyzed sulfuric acid solution is monitored online, and
   wherein in the measurement of the overall concentration of the oxidizing substances, part of the electrolyzed sulfuric acid solution is branched as the sample liquid at any intermediate position of a supply line through which the electrolyzed sulfuric acid solution is supplied for the substrate cleaning to measure the overall concentration of the oxidizing substances.

2. The substrate cleaning method according to claim 1, wherein the part of the electrolyzed sulfuric acid solution is branched as the sample liquid from the substrate cleaning system for absorbance measurement before the electrolyzed sulfuric acid solution comes into contact with the substrate, and the sample liquid after the measurement is returned to the substrate cleaning system.

3. The substrate cleaning method according to claim 1, wherein waste of a cleaning liquid used to clean the substrate is not circulated to be reused but is discarded, the part of the electrolyzed sulfuric acid solution is branched as the sample liquid at any intermediate position of the supply line through which the electrolyzed sulfuric acid solution is supplied for the substrate cleaning from a line through which the electrolyzed liquid is circulated, the absorbance measurement is performed on the sample liquid to measure the overall concentration of the oxidizing substances, and after the measurement, in a position upstream of the substrate being cleaned, the sample liquid is returned to the substrate cleaning system.

4. The substrate cleaning method according to claim 3, wherein the electrolyzed sulfuric acid solution after the measurement is returned to a position upstream of the position where the electrolyzed sulfuric acid solution is branched from the supply line.

5. The substrate cleaning method according to claim 1, wherein the oxidizing substances include peroxomonosulfuric acid, peroxodisulfuric acid, and hydrogen peroxide.

* * * * *